United States Patent [19]

Warnant et al.

[11] 4,133,826

[45] Jan. 9, 1979

[54] NOVEL INVERSION PROCESS

[75] Inventors: Julien Warnant, Neuilly-sur-Seine; Jacques Marechal-Prost, Paris; Philippe Cosquer, Saint-Denis, all of France

[73] Assignee: Roussel UCLAF, Paris, France

[21] Appl. No.: 789,774

[22] Filed: Apr. 22, 1977

[30] Foreign Application Priority Data

Apr. 23, 1976 [FR] France ................. 76 12094

[51] Int. Cl.$^2$ .......................... C07C 121/75
[52] U.S. Cl. ............................. 260/465 D
[58] Field of Search .............. 260/465 D; 560/124

[56] References Cited

U.S. PATENT DOCUMENTS

| 3,046,299 | 7/1962 | Julia ........................... 560/124 |
| 3,786,070 | 1/1974 | Martel et al. ............... 560/124 |
| 3,906,026 | 9/1975 | Nagase et al. ............. 560/124 |

FOREIGN PATENT DOCUMENTS 2240914  3/1975  France.

*Primary Examiner*—Elbert L. Roberts
*Assistant Examiner*—Molly C. Eakin
*Attorney, Agent, or Firm*—Hammond & Littell

[57] ABSTRACT

A process for the preparation of an ester of chiral (A) acid with an optically active (S) α-cyano-3-phenoxybenzyl alcohol by reacting an ester of chiral (A) acid with α-cyano-3-phenoxybenzyl alcohol of the formula

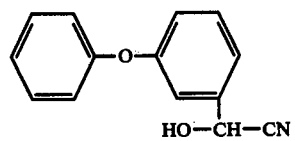

B in its optically active (R) form or a racemic (R,S) mixture or a mixture of esters of said (R) alcohol and (S) alcohol in non-equimolecular proportions designated herein as "ester (R+S)" with a base selected from the group consisting of ammonium hydroxide, primary, secondary and tertiary amines, quaternary ammonium compounds, liquid amines of high molecular weight, ion exchange resins of a basic character and a catalytic amount of a strong base in at least one solvent in which the ester of the (R) alcohol is soluble and in which the ester of the (S) alcohol is insoluble and recovering from the resulting medium the chiral (A) acid ester of the (S) alcohol which is insoluble.

25 Claims, No Drawings

NOVEL INVERSION PROCESS

STATE OF THE ART

French Pat. No. 2,240,914 describes insecticides of the pyrethrin type.

OBJECTS OF THE INVENTION

It is an object of the invention to provide novel processes for the preparation of esters of chiral (A) acid and α-cyano-3-phenoxybenzyl alcohol of the (S) structure in a simple, economical fashion.

This and other objects and advantages of the invention will become obvious from the following detailed description.

THE INVENTION

The novel process of the invention for the preparation of esters of chiral (A) acids and (S) α-cyano-3-phenoxybenzyl alcohol comprises reacting an ester of a chiral (A) acid with α-cyano-3-phenoxybenzyl alcohol of the formula

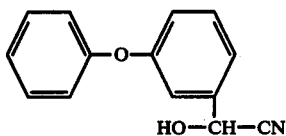

in its optically active (R) form or a racemic (R,S) mixture or a mixture of esters of said (R) alcohol and (S) alcohol in non-equimolecular proportions with a base selected from the group consisting of ammonium hydroxide, primary, secondary and tertiary amines, quaternary ammonium compounds, liquid amines of high molecular weight, ion exchange resins of a basic character and a catalytic amount of a strong base in at least one solvent in which the ester of the (R) alcohol is soluble and in which the ester of the (S) alcohol is insoluble and recovering from the resulting medium the chiral (A) acid ester of the (S) alcohol which is insoluble. This process is called process α'.

The invention has particularly as object a process which comprises reacting an ester of a chiral (A) acid with an (R) optically active isomer of α-cyano-3-phenoxybenzyl alcohol or a racemic (R,S) mixture or a mixture in nonequimolecular ratios of esters of a chiral (A) acid with (R) and (S) isomers of α-cyano-3-phenoxybenzyl alcohol with a basic agent selected from the group consisting of ammonium hydroxide, secondary or tertiary amines and a catalytic amount of strong bases in at least one solvent in which the ester of the (S) alcohol is insoluble and the ester of the (R) alcohol is soluble and then recovering from the reaction medium the ester of chiral (A) acid and the (S) alcohol which is insoluble. This process is called process α.

The chiral (A) acid may possess an asymetric carbon atom.

Thus, the invention has as object a process conforming to general process α' and particularly general process α, characterized in that the chiral (A) acid is an acid possessing an asymetric carbon atom. The chiral (A) acid equally may be an acid possessing 2 asymetric carbon atoms, particularly a cyclopropane carboxylic acid in which two of the carbon atoms of the ring are asymetric carbon atoms.

Thus, the invention has as the object a process conforming to general process α' and notably general process α, characterized in that the chiral (A) acid is an acid possessing 2 asymetric carbon atoms and more particularly a process conforming to general process α' and particularly general process α, characterized in that the chiral (A) acid is a cyclopropane carboxylic acid with 2 carbon atoms of the ring being asymetrical.

The chiral (A) cyclopropane carboxylic acids optically active, of cis or trans structure, possessing asymetric carbon atoms in the 1- and 3-positions are the preferred cyclopropane carboxylic acid and have the formula

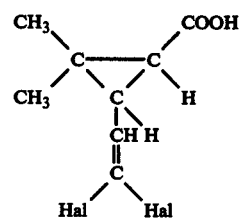

wherein Hal is chlorine or bromine. Using a simple nomenclature, the acids of 1R, 3R structure are designated as (1R, cis) acids and acids of the 1R, 3S structure are designated as (1R, trans) acids. Among the preferred chiral cyclopropane carboxylic acids are 2,2-dimethyl-3R-(2,2-dibromovinyl)-cyclopropane-1R-carboxylic acid or 1R, cis 2,2-dimethyl-3-(2,2-dibromovinyl)-cyclopropane carboxylic acid and 2,2-dimethyl-3R-(2,2-dichlorovinyl)-cyclopropane-1R-carboxylic acid or 1R, cis 2,2-dimethyl-3-(2,2-dichlorovinyl)-cyclopropanecarboxylic acid.

The basic agent used in the general process α of the invention in the presence of which is effected the transformation into the esters of the (S) alcohol is preferably selected from the group consisting of ammonium hydroxide, triethylamine, diethylamine, pyrrolidine, morpholine, piperidine and the strong bases which are used in catalytic amounts such as sodium hydroxide, potassium hydroxide, alkali metal alcoholates, alkali metal amides and alkali metal hydrides.

However, the list of said bases is not intended to be limiting and other bases of analogous strength may be used without departing from the scope of the invention such as diisopropylamine, ephedrine, triethylenediamine and catalytic amounts of potassium tert.-butylate or sodium isopropylate. The preferred basic agents are ammonium hydroxide and triethylamine.

The basic agent used in the general process α' of the invention in which is effected the transformation into an ester of the (S) alcohol is preferably selected from the group consisting of ammonium hydroxide, triethylamine, diethylamine, pyrrolidine, morpholine, piperidine and strong bases used in catalytic amounts such as sodium hydroxide, potassium hydroxide, alkali metal alcoholates, alkali metal amides and alkali metal hydrides. The above list of preferred bases for the process of the invention is not intended to be limiting. Other bases of analogous strength may be used without departing from the scope of the invention.

Among the other bases useful for the process are diisopropylamine, ephedrine, triethylenediamine and catalytic amounts of potassium tert.-butylate or sodium isopropylate. Other basic agents include benzylamine, n-butylamine, sec-butylamine, tetrabutylammonium hydroxide and ion exchange resins of a strong basic character comprising quaternary ammoniums or amines. Resins of this type are sold under the tradenames Dowex and Amberlite such as Dowex AGIX8, Amberlite IRA 400 or Amberlite IR 45. Also useful as the basic agents are high molecular weight liquid amines which are insoluble in water such as the "liquid Amberlites" which are commerically sold such as liquid Amberlites of the type LA1 or LA2.

The solvent or mixture of solvents used in the process α' and notably process α are preferably selected from the group consisting of acetonitrile, alkanols, mixtures of alkanols and petroleum ether, notably mixtures of an alkanol and pentane, hexane or heptane and most preferred are acetonitrile, propanol, isopropanol, straight and branch chained butanols and mixtures of the said alkanols with essence G, essence B, essence C, essence E, pentane, hexane or heptane. Isopropanol is particularly interesting for the transformation of the process.

It is evident that the term "insoluble" for the esters of the (S) alcohol and "soluble" for the ester of the (R) alcohol are taken in their current acceptance. In the solvents used in the process, the esters of the (S) alcohol present a certain solubility which must be weak enough to obtain a good yield taking into account the volume of solvent used. In practice, the solvent or mixture of solvents as well as the volume of the solvents permit the obtaining of a weight yield of at least 80% of the ester of the (S) alcohol. The preceding list of solvents and solvent mixtures is not intended to be limiting as other solvent systems may be used.

The esters of the (R) alcohol are in general very soluble in the solvents used in the process described above and a limited volume of solvent permits total solubilization.

The reaction temperature influences the rate of the reaction and the reaction time is notably a function of the temperature and the nature of the base used.

Among the chiral (A) acids of the cyclopropane carboxylic acid type, the preferred acid of the invention is 2,2-dimethyl-3R-(2,2-dibromovinyl)-cyclopropane-1R-carboxylic acid or 1R, cis 2,2-dimethyl-3-(2,2-dibromovinyl)-cyclopropane-carboxylic acid.

The invention has for its object a process for the transformation according to process α' characterized in that an ester of 2,2-dimethyl-3R-(2,2-dibromovinyl)-cyclopropane-1R-carboxylic acid and the optically active (R) isomer of α-cyano-3-phenoxybenzyl alcohol or a racemic (R,S) mixture or a mixture of the (R) and (S) isomer of non-equimolar proportions is subjected to a basic agent selected from the group consisting of ammonium hydroxide, primary, secondary and tertiary amines, quaternary ammonium compounds, ion exchange resins of a basic nature, high molecular weight liquid amines and a catalytic amount of a strong base in one or more solvents in which the ester of the (R) alcohol is soluble and in which the ester of the (S) alcohol is insoluble and then isolating from the reaction medium the insoluble ester of 2,2-dimethyl-3R-(2,2-dibromovinyl)-cyclopropane-1R-carboxylic acid and (S) α-cyano-3-phenoxybenzyl alcohol. This process is called the β'-process.

The invention also concerns a process conforming to general process α which will be designated as β, comprising subjecting an ester of 2,2-dimethyl-3R-(2,2-dibromovinyl)-cyclopropane-1R-carboxylic acid with (R) α-cyano-3-phenoxybenzyl alcohol or the (R,S) racemic mixture or a mixture of the (R) and (S) isomers in non-equimolar amounts to a basic agent selected from the group consisting of ammonium hydroxide, secondary and tertiary amines and a catalytic amount of a strong base in one or more solvents in which the ester of the (S) alcohol is insoluble and the ester of the (R) alcohol is soluble and recovering from the reaction medium the ester of the (S) alcohol which is insoluble.

The preferred basic agents and the solvents for use in process β and β' to effect the transformation to the ester of the (S) alcohol are preferably the same as those discussed above for process α and α'.

The invention especially has for its object a process conforming to process β for transforming (R) α-cyano-3-phenoxybenzyl 2,2-dimethyl-3R-(2,2-dibromovinyl)-cyclopropane-1R-carboxylate into (S) α-cyano-3-phenoxybenzyl 2,2-dimethyl-3R-(2,2-dibromovinyl)-cyclopropane-1R-carboxylate comprising reacting the starting ester of the (R) alcohol with a basic agent selected from the group consisting of ammonium hydroxide, secondary and tertiary amines and catalytic amounts of a strong base in a solvent selected from the group consisting of acetonitrile, alkanols and mixtures of alkanols and petroleum ether, especially mixtures of an alkanol and pentane, hexane or heptane which process is designated γ. The preferred base in process γ is ammonium hydroxide or triethylamine and the solvent is preferably isopropanol.

The invention also has a process conforming to process β' in which the said transformation is effected starting from the ester of the (R) alcohol and it will be designated γ'.

Another embodiment of the process of the invention conforming to process β for transforming racemic (R,S) α-cyano-3-phenoxybenzyl 2,2-dimethyl-3R-(2,2-dibromovinyl)-cyclopropane-1-R-carboxylate into (S) α-cyano-3-phenoxybenzyl 2,2-dimethyl-3R-(2,2-dibromovinyl)-cyclopropane-1R-carboxylate comprises reacting the ester of the racemic (R,S) alcohol with a basic agent selected from the group consisting of ammonium hydroxide, secondary and tertiary amines and catalytic amounts of a strong base in a solvent selected from the group consisting of acetonitrile, alkanols and mixtures of alkanols and petroleum ether, especially mixtures of an alkanol and pentane, hexane or heptane which process is designated δ. In process δ, the preferred basic agent is ammonium hydroxide or triethylamine and the preferred solvent is isopropanol.

The invention also has as object a process conforming to process β' wherein the ester of the racemic (R,S) alcohol is transformed into the ester of the (S) alcohol which will be designated process δ'.

The invention also has for its object a process conforming to process β which will be designated ε for transforming a mixture of (R) α-cyano-3-phenoxybenzyl 2,2-dimethyl-3R-(2,2-dibromovinyl)-cyclopropane-1R-carboxylate and (S) α-cyano-3-phenoxybenzyl 2,2-dimethyl-3R-(2,2-dibromovinyl)-cyclopropane-1R-carboxylate in non-equimolar proportions into (S) α-cyano-3-phenoxybenzyl 2,2-dimethyl-3R-(2,2-dibromovinyl)-cyclopropane-1R-carboxylate comprising reacting the starting mixture of esters with a strong base selected from the group consisting of ammonium hydroxide, secondary and tertiary amines and a catalytic amounts of a strong base in a solvent selected from the group consisting of acetonitrile, alkanols and mixtures of alkanols and petroleum ether, especially mixtures of an alkanol and pentane, hexane or heptane. In process ε, the preferred base is ammonium hydroxide or triethylamine and the solvent is preferably isopropanol.

The invention equally has for its object a process conforming to process β' in which the said "ester (R+S)" is transformed into the ester of the (S) alcohol which is designated process ε'.

The invention also has as object a process conforming to process α wherein the ester of 2,2-dimethyl-3R-(2,2-dichlorovinyl)-cyclopropane-1R-carboxylic acid with (R) α-cyano-3-phenoxybenzyl alcohol or a racemic (R,S) or a mixture of (R) and (S) forms of the said alcohol in non-equimolar proportions designated herein as "dichloro (R+S) ester" into the ester of the said acid and the (S) alcohol comprising reacting the ester of the (R) alcohol or the racemic (R,S) alcohol or the "dichloro (R+S) ester" with a basic agent selected from the group consisting of ammonium hydroxide, secondary and tertiary amines and a catalytic amount of a strong base in a solvent or mixture of solvents in which the ester of the (S) alcohol is insoluble and the ester of the (R) alcohol is soluble and isolating from the reaction medium the ester of the (S) alcohol which is insoluble. This process is designated $\beta_1$.

The invention equally has as object a process conforming to process α' wherein the chiral (A) acid is 2,2-dimethyl-3R-(2,2-dichlorovinyl)-cyclopropane-1R-carboxylic acid which will be designated process $\beta_1'$.

The basic agent and the solvent or mixture of solvents preferably used in process $\beta_1'$ and notably in process $\beta_1$ are identical to the basic agents and solvents mentioned above for processes α' and α.

The invention also has as object a process conforming to process $\beta_1$ for transforming (R) α-cyano-3-phenoxybenzyl 2,2-dimethyl-3R-(2,2-dichlorovinyl)-cyclopropane-1R-carboxylate into (S) α-cyano-3-phenoxybenzyl 2,2-dimethyl-3R-(2,2-dichlorovinyl)-cyclopropane-1R-carboxylate comprising reacting the ester of the (R) alcohol with a basic agent selected from the group consisting of ammonium hydroxide, secondary and tertiary amines and a catalytic amount of a strong base in a solvent selected from the group consisting of acetonitrile, alkanols and mixtures of alkanols and petroleum ether, especially mixtures of an alkanol and pentane, hexane or heptane. The said process is designated $\gamma_1$. Preferably the basic agent is ammonium hydroxide or triethylamine and the solvent is isopropanol.

The invention also has as object a process conforming to process $\beta_1'$ wherein the transformation is effected with the ester of the R alcohol which will be designated as process $\gamma_1'$.

The invention also has as object a process conforming to process $\beta_1$ for transforming (R,S) α-cyano-3-phenoxybenzyl 2,2-dimethyl-3R-(2,2-dichlorovinyl)-cyclopropane-1R-carboxylate into the ester of the (S) alcohol comprising reacting the ester of the racemic alcohol with a basic agent selected from the group consisting of ammonium hydroxide, secondary and tertiary amines and a catalytic amount of a strong base in a solvent selected from the group consisting of acetonitrile, alkanols and mixtures of alkanols and petroleum ether, especially mixtures of an alkanol and pentane, hexane or heptane. This process is designated as process $\delta_1$ and the preferred base is ammonium hydroxide or triethylamine and the preferred solvent is isopropanol.

The invention also has as object a process conforming to process $\beta_1'$, wherein the transformation is effected with the ester of the racemic (R,S) alcohol, which will be designated process $\delta_1'$.

The invention also has as object a process conforming to process $\beta_1$ for transforming (R) α-cyano-3-phenoxybenzyl 2,2-dimethyl-3R-(2,2-dichlorovinyl)-cyclopropane-1R-carboxylate and (S) α-cyano-3-phenoxybenzyl 2,2-dimethyl-3R-(2,2-dichlorovinyl)-cyclopropane-1R-carboxylate [dichloro (R+S) ester] into the ester of the (S) alcohol comprising reacting the dichloro (R+S) ester with a basic agent selected from the group consisting of ammonium hydroxide, secondary and tertiary amines and a catalytic amount of a strong base in a solvent selected from the group consisting of acetonitrile, alkanols and mixtures of alkanols and petroleum ether, especially mixtures of an alkanol and pentane, hexane or heptane. This process is designated as process $\epsilon_1$ and the preferred base is ammonium hydroxide or triethylamine and the preferred solvent is isopropanol.

The invention also has as object a process conforming to process $\beta_1'$ wherein the transformation is effected on the dichloro (R+S) ester which process is designated $\epsilon_1'$.

The mechanism of the reaction may be explained in the following manner:

By the action of a base of suitable strength which in practice is selected from the group consisting of ammonium hydroxide, primary, secondary and tertiary amines, ion exchange resins of a basic character, high molecular weight liquid amines and a catalytic amount of a strong base, the ester of the chiral (A) acid and the (R) alcohol contained in the starting material produces a α-cyano-carbanion which leads to racemization of the corresponding carbon atoms.

The subsequent protonation in the solvent or mixture of solvents leads in the soluble fraction to the formation in equimolecular proportions to the 2 diasteroisomers [ester of the (S) alcohol and ester of the (R) alcohol] by the following reaction scheme:

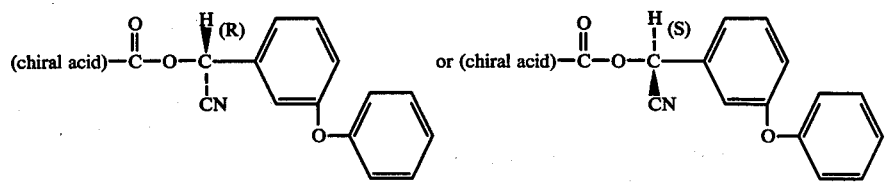

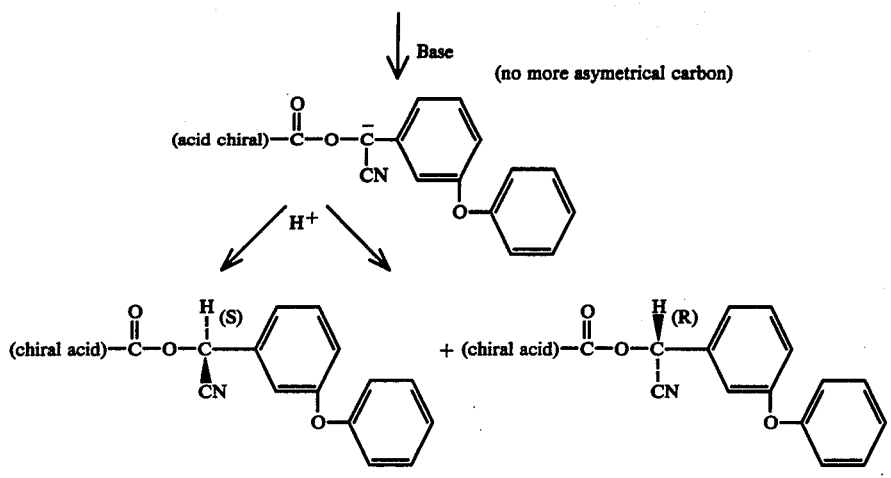

In the solvent or mixture of solvents used in the process, the esters of the chiral (A) acid and the (S) alcohol are insoluble and the esters of the chiral (A) acid and the (R) alcohol are soluble so that the equilibrium is displaced towards the formation of the ester of the (S) alcohol and in practice leads to yields of 80 to 90% of the ester of the (S) alcohol based on starting optically active ester placed in action.

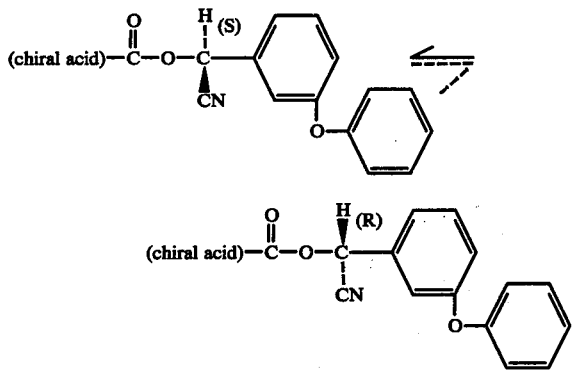

The intermediate formation of the mixture of the esters of the (R) and (S) alcohol in equimolar proportions can be shown by evaporation to dryness of the soluble fraction. The process of racemization occurs in practically quantitative yields, which is contrary to the case of the present invention, when the solvent or mixture of solvents selected is a solvent for the ester of the (R) alcohol and the ester of the (S) alcohol and racemic mixture of the (R,S) alcohol as described in our copending application Ser. No. 789,843 filed on even date herewith.

This theoretical explanation is merely an attempt to explain the results observed and is not intended to limit the invention in any fashion.

The process of the invention presents a particularly unexpected character because in so far as what was known, the transformation process of an ester of an optically active alcohol into an ester of an optically active alcohol of antipodal structure which occurs in practically quantitative yields was not known.

The process of the invention is particularly interesting when the chiral acids used are the optically active cyclopropane carboxylic acids of the 1R,3R (or 1R cis) or the 1R,3S (1R, trans) structure of the formula

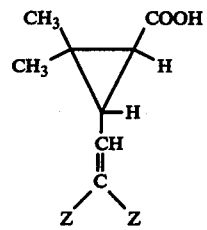

wherein Z is bromine or chlorine.

In effect for the last few years, insecticidal compounds with an exceptionally high activity have been prepared by esterifying the above chiral acids with α-cyano-3-phenoxybenzyl alcohols.

It has been established that in a general way the esters of the above chiral acids and the (S) α-cyano-3-phenoxybenzyl alcohol possess a much greater insecticidal activity than the corresponding esters of the (R,S) racemic alcohol or the (R) optical isomer of the alcohol. The α-cyano-3-phenoxybenzyl alcohol is obtained synthetically in a racemic form and the fragility of the molecule does not permit a stereoselective preparation of the enantiomeres nor the resolution of the racemic alcohol.

To obtain esters of the alcohol of the (S) configuration, the only procedure known to now consisted of effecting a separation of an ester of the (R) form and an ester of the (S) form of the alcohol by selective insolubilization of the last in a suitable solvent which leads to yields of esters of the (S) alcohol less than 50% with respect to the ester of the racemic alcohol used.

The ester of the (R) alcohol or mixtures of esters of the (R) and (S) alcohols, rich in the ester of the (R) alcohol thus arising from the preparation of the ester of the (S) alcohol appear to be less interesting residues of the preparation of esters of the (S) alcohol.

The process of the invention now permits the direct transformation in practically quantitative yields either of the esters of 2,2-dimethyl-3R-(2,2-dibromovinyl)-cyclopropane-1R-carboxylic acid or 2,2-dimethyl-3R-(2,2-dichlorovinyl)-cyclopropane-1R-carboxylic acid and α-cyano-3-phenoxybenzyl alcohol in its (R,S) racemic form or of the esters of the alcohol in its (R) form or of the mixture of esters of alcohol in its (R) and (S)

forms in non-equimolecular proportion and especially the mixtures rich in ester of the (R) alcohol, into the ester of the (S) alcohol.

The process of the invention includes a single step, needs only simple manipulations and uses relatively inexpensive reactants and permits the obtention with very high yields under particularly advantageous conditions of the esters of cyclopropane carboxylic acids described above containing a dichlorovinyl or a dibromovinyl chain with (S) α-cyano-3-phenoxybenzyl alcohol which has exceptionally high insecticidal activity.

(S) α-cyano-3-phenoxybenzyl 2,2-dimethyl-3R-(2,2-dichlorovinyl)-cyclopropane-1R-carboxylate and (R) α-cyano-3-phenoxybenzyl 2,2-dimethyl-3R-(2,2-dichlorovinyl)-cyclopropane-1R-carboxylate are not described in the literature.

(S) α-cyano-3-phenoxybenzyl 2,2-dimethyl-3R-(2,2-dichlorovinyl)-cyclopropane-1R-carboxylate has excellent insecticidal activity and is particularly useful in the agricultural field for combatting insects. For example, the said product is effective against aphis larvae of Lepidoptera and coleoptera and is equally useful as a household insecticide for flies or mosquitoes. Experimental tests have shown the product to be effective against domestic flies and larvae of Spodoptera Littoralis.

The insecticidal compositions of the invention are comprised of an insecticidally effective amount of at least one compound of the group consisting of (R) α-cyano-3-phenoxybenzyl 2,2-dimethyl-3R-(2,2-dichlorovinyl)-cyclopropane-1R-carboxylate and (S) α-cyano-3-phenoxybenzyl 2,2-dimethyl-3R-(2,2-dichlorovinyl)-cyclopropane-1R-carboxylate and an inert carrier. The esters of the (S) alcohols have a greater insecticidal activity than the esters of the (R) alcohol. The compositions may preferably contain 0.005 to 10% by weight of the active compounds and may contain one or more other pesticidal agents. The compositions may be in the form of powders, granules, suspensions, emulsions, solutions, aerosol compositions, combustible tapes, coils, or other classically used preparation for the use of compounds of this nature.

Examples of the inert carriers of the compositions of the invention are a vehicle and/or a non-ionic surface active agent to ensure a uniform dispersion of the substance making up the composition. The vehicle may be a liquid such as water, alcohol, hydrocarbons, other organic solvents or a mineral, animal or vegetable oil or a powdered solid such as talc, clays, silicates, kieselguhr or a combustible solid such as tabu powder (or pyrethrum residue).

To increase the insecticidal activity, the compositions may also contain a classic synergist for pyrethrum compounds such as 1-(2,5,8-trioxadodecyl-2-propyl-4,5-methylenedioxy)-benzene (or piperonyl butoxide), N-(2-ethylheptyl)-bicyclo-[2,2,1]-5-heptene-2,3-dicarboximide and piperonylbis-2-(2'-n-butoxyethoxy)-ethyl acetal (tropital).

The novel method of the invention of combatting insects comprises contacting the insects with an insecticidally effective amount of at least one compound of the group consisting of (R) α-cyano-3-phenoxybenzyl 2,2-dimethyl-3R-(2,2-dichlorovinyl)-cyclopropane-1R-carboxylate and (S) α-cyano-3-phenoxybenzyl 2,2-dimethyl-3R-(2,2-dichlorovinyl)-cyclopropane-1R-carboxylate. The preferred compound is the ester of the (S) alcohol.

In the following examples there are described several preferred embodiments to illustrate the invention. However, it is to be understood that the invention is not intended to be limited to the specific embodiments.

EXAMPLE 1

1 g of (R) α-cyano-3-phenoxybenzyl 2,2-dimethyl-3R-(2,2-dibromovinyl)-cyclopropane-1R-carboxylate with a specific rotation of $[\alpha]_D^{20} = -30.5°$ (c = 1% in benzene) and $-25.5°$ (c = 1% in chloroform) was added to 2.5 ml of isopropanol and then 0.15 ml of aqueous 22° Bé ammonium hydroxide was added thereto. The mixture was stirred at 20° C. for 18 hours and was then vacuum filtered. The recovered product was washed and dried to obtain 0.9 g of (S) α-cyano-3-phenoxybenzyl 2,2-dimethyl-3R-(2,2-dibromovinyl)-cyclopropane-1R-carboxylate melting at 100° C. and having a specific rotation of $[\alpha]_D^{20} = +60.5°$ (c = 1% in benzene) and $+25°$ (c = 1% in chloroform).

Analysis: $C_{22}H_{19}O_3NBr_2$; molecular weight = 502.2:
Calculated: %C 52.3 %H 3.79 %N 2.77 %Br 31.63:
Found: 52.2 4.0 2.7 31.5.

EXAMPLE 2

Using the procedure of Example 1 but with 0.30 ml of aqueous 22° Bé ammonium hydroxide solution, 1 g of the ester of the (R) alcohol was reacted to obtain 0.9 g of (S) α-cyano-3-phenoxybenzyl 2,2-dimethyl-3R-(2,2-dibromovinyl)-cyclopropane-1R-carboxylate of the same quality as in Example 1.

EXAMPLE 3

Using the procedure of Example 1 but with 0.16 g of triethylamine as the base, 1 g of the ester of the (R) alcohol was reacted to obtain 0.87 g of the ester of the (S) alcohol of the same quality as in Example 1.

EXAMPLE 4

Using the procedure of Example 1 but with 0.32 g of triethylamine as the base, 1 g of the ester of the (R) alcohol was reacted to obtain 0.9 g of the ester of the (S) alcohol of the same quality as in Example 1.

EXAMPLE 5

Using the procedure of Example 1 but with 0.11 g of pyrrolidine as the base, 1 g of the ester of the (R) alcohol was reacted to obtain 0.80 g of the ester of the (S) alcohol of the same quality as in Example 1.

EXAMPLE 6

Using the procedure of Example 1 but with 0.13 g of morpholine as the base, and with stirring at 20° C. for 96 hours 1 g of the ester of the (R) alcohol was reacted to obtain 0.9 g of the ester of the (S) alcohol of the same quality as in Example 1.

EXAMPLE 7

Using the procedure of Example 1 but with 0.008 g of sodium hydroxide as the base, 1 g of the ester of the (R) alcohol was reacted to obtain 0.85 g of the ester of the (S) alcohol of the same quality as in Example 1.

EXAMPLE 8

Using the procedure of Example 1 but with 2.5 ml of isopropanol as the solvent, 1 g of the ester of the (R) alcohol was reacted to obtain 0.80 g of the ester of the (S) alcohol of the same quality as in Example 1.

EXAMPLE 9

Using the procedure of Example 1 but with 2.5 ml of tert.-butanol as the solvent, 1 g of the ester of the (R) alcohol was reacted to obtain 0.85 g of the ester of the (S) alcohol of the same quality as in Example 1.

EXAMPLE 10

0.15 ml of aqueous 22° Bé ammonium hydroxide was added to a solution of 1g of (R) α-cyano-3-phenoxybenzyl 2,2-dimethyl-3R-(2,2-dibromovinyl)-cyclopropane-1R-carboxylate in 2 ml of acetonitrile and 0.5 ml of water and the mixture was stirred at 20° C. for 18 hours. The mixture was vacuum filtered and the solid product was washed with acetonitrile containing 25% water and was dried to obtain 0.87 g of the ester of the (S) alcohol of the same quality as in Example 1.

EXAMPLE 11

Using the procedure of Example 9 with 2.5 ml of tert.-butanol and 0.16 g of triethylamine as the base, 1 g of the ester of the (R) alcohol was reacted to obtain 0.8 g of the ester of the (S) alcohol of the same quality as in Example 1.

EXAMPLE 12

Using the procedure of Example 8 but with 0.11 g of pyrrolidine as the base, 1 g of the ester of the (R) alcohol was reacted to obtain 0.8 g of the ester of the (S) alcohol of the same quality as in Example 1.

EXAMPLE 13

15 ml of aqueous 22° Bé ammonium hydroxide solution were added to a solution of 105 g of (R,S) α-cyano-3-phenoxybenzyl 2,2-dimethyl-3R-(2,2-dibromovinyl)-cyclopropane-1R-carboxylate with a specific rotation of $[\alpha]_D^{20} = 0°-1°$ (c = 1% in chloroform) and +14° (c = 1% in benzene) in 262.5 ml of isopropanol and the mixture was stirred at 20° C. for 18 hours. The mixture was vacuum filtered and the recovered precipitate was washed with 105 ml of isopropanol and was dried to obtain 95.1 g of (S) α-cyano-3-phenoxybenzyl 2,2-dimethyl-3R-(2,2-dibromovinyl)-cyclopropane-1R-carboxylate with a melting point of 100° C. and a specific rotation of $[\alpha]_D^{20} = +60.5°$ (c = 1% in benzene) of the same quality as in Example 1.

EXAMPLE 14

0.30 ml of aqueous 22° Bé ammonium hydroxide solution was added to a solution of 1 g of the (R,S) α-cyano-3-phenoxybenzyl 2,2-dimethyl-3R-(2,2-dibromovinyl)-cyclopropane-1R-carboxylate in 2.5 ml of isopropanol and the mixture was stirred at 20° C. for 20 hours. The mixture was then vacuum filtered and the recovered product was washed with 1 ml of isopropanol and was dried to obtain 0.9 g of the ester of the (S) alcohol of the same quality as in Example 1.

EXAMPLE 15

0.16 g of triethylamine was added to a solution of 1 g of (R,S) α-cyano-3-phenoxybenzyl 2,2-dimethyl-3R-(2,2-dibromovinyl)-cyclopropane-1R-carboxylate in 2.5 ml of isopropanol and the mixture was stirred for 15 hours at 20° C. The mixture was vacuum filtered and the recovered product was washed with 1 ml of isopropanol and was dried to obtain 0.87 g of the ester of the (S) alcohol of the same quality as in Example 1.

EXAMPLE 16

Using the procedure of Example 15 but with 0.32 g of triethylamine as the base, 1 g of the ester of the (R,S) alcohol was reacted to obtain 0.9 g of the ester of the (S) alcohol of the same quality as in Example 1.

EXAMPLE 17

Using the procedure of Example 15 but with 0.13 g of morpholine as the base, 1 g of the ester of the (R,S) alcohol was reacted to obtain 0.9 g of the ester of the (S) alcohol of the same quality as in Example 1.

EXAMPLE 18

Using the procedure of Example 15 but with 0.008 g of sodium hydroxide as the base and stirring for 18 hours, 1 g of the ester of the (R,S) alcohol was reacted to obtain 0.85 g of the ester of the (S) alcohol of the same quality as in Example 1.

EXAMPLE 19

0.15 g of aqueous 22° Bé ammonium hydroxide solution was added to a solution of 1 g of (R,S) α-cyano-3-phenoxybenzyl 2,2-dimethyl-3R-(2,2-dibromovinyl)-cyclopropane-1R-carboxylate in 2 ml of acetonitrile and 0.5 ml of water and the mixture was stirred at 20° C. for 17 hours. The mixture was vacuum filtered and the recovered product was washed with acetonitrile containing 25% water and was dried to obtain 0.87 g of the ester of the (S) alcohol of the same quality as in Example 1.

EXAMPLE 20

A mixture of 10 g of (R,S) α-cyano-3-phenoxybenzyl 2,2-dimethyl-3R-(2,2-dibromovinyl)-cyclopropane-1R-carboxylate with a specific rotation of $[\alpha]_D^{20} = 0°$ to −1° (c = 1% in chloroform) and +14° (c = 1% in benzene) in 20 ml of isopropanol was stirred for 18 hours at 20° C. and was then vacuum filtered. The recovered product was washed with 10 ml of isopropanol and was dried to obtain 4 g of the ester of the (S) alcohol with a specific rotation of $[\alpha]_D^{20} = +60°$ (c = 1% in benzene) and a melting point of 100° C.

The combined filtrate and wash water designated as solution L contained 5 g of the ester of the (R) alcohol and 1 g of the ester of the (S) alcohol and 0.8 ml of aqueous 22° Bé ammonium hydroxide was added to solution L which was then stirred at 20° C. for 20 hours. The mixture was vacuum filtered and the recovered precipitate was washed with 5 ml of isopropanol and dried to obtain 4.5 g of the ester of the (S) alcohol with a melting point of 100° C. and a specific rotation of $[\alpha]_D^{20} = +60°$ (c = 1% in benzene) of the same quality as in Example 1.

EXAMPLE 21

10 g of (R,S) α-cyano-3-phenoxybenzyl 2,2-dimethyl-3R-(2,2-dichlorovinyl)-cyclopropane-1R-carboxylate with a specific rotation of $[\alpha]_D^{20} = +16.5°$ (c = 10% in benzene) were chromatographed over silica gel and elution with a 85-15 petroleum ether. (B.p. = 40°-70° C.)-isopropyl ether mixture yielded 3 g of (R) α-cyano-3-phenoxybenzyl 2,2-dimethyl-3R-(2,2-dichlorovinyl)-cyclopropane-1R-carboxylate with a specific rotation of $[\alpha]_D^{20} = -31°$ (c = 1% in benzene) and −21.5° (c = 1% in chloroform).

60 g of the said product were admixed with 120 ml of isopropanol and then 9 ml of aqueous 22° Bé ammonium hydroxide solution were added thereto. The mixture was stirred at 0° C. for 48 hours and was then vacuum filtered. The recovered product was then washed with 30 ml of isopropanol at −20° C. and dried to obtain 48.5 g of the ester of the (S) alcohol melting at 60° C. and having a specific rotation of $[\alpha]_D^{20} = +66°$ (c = 1% in benzene) and +34° (c = 1% in chloroform).

EXAMPLE 22

90 ml of aqueous 22° Bé ammonium hydroxide solution were added to a solution of 600 g of (R,S) α-cyano-3-phenoxybenzyl 2,2-dimethyl-3R-(2,2-dichlorovinyl)-cyclopropane-1R-carboxylate in 1200 ml of isopropanol and the mixture was stirred at 0° C. for 48 hours and was vacuum filtered. The recovered precipitate was washed with 300 ml of isopropanol at −20° C. and dried to obtain 485 g of the ester of the (S) alcohol melting at 60° C. and having a specific rotation of $[\alpha]_D^{20} = +66°$ (c = 1% in benzene) and +34° (c = 1% in chloroform).

Analysis: $C_{22}H_{19}O_3NCl_2$; molecular weight = 416.28: Calculated: %C 63.48 %H 4.60 %N 3.36 Cl% 17.03: Found: 63.7 4.6 3.4 17.1.

EXAMPLE 23

0.8 g of diisopropylamine was added to a solution of 10 g of (R,S) α-cyano-3-phenoxybenzyl 2,2-dimethyl-3R-(2,2-dibromovinyl)-cyclopropane-1R-carboxylate with a specific rotation of $[\alpha]_D^{20} = 0°$ to −1° C. (c = 1% in chloroform) and +14° (c = 1% in benzene) in 25 ml of isopropanol and the mixture was stirred for 6 hours at 20° C. and 2 hours at 0° C. The mixture was vacuum filtered and the recovered product was crystallized from 2 volumes of isopropanol to obtain 8.04 g of the ester of the (S) alcohol with a specific rotation of $[\alpha]_D^{20} = +57°$ (c = 4% in toluene).

EXAMPLE 24

Using the procedure of Example 23, the process was repeated except for stirring for 48 hours at 0° C. to obtain the same yield of the ester of the (S) alcohol of the same quality as in Example 23.

EXAMPLE 25

Using the process of Example 23 but with isopropanol containing 3.5% water as the solvent and stirring for 8 hours at 20° C., there were obtain 8.16 g of the ester of the (S) alcohol with a specific rotation of $[\alpha]_D^{20} = +56.5$ (c = 4% in toluene).

EXAMPLE 26

1.39 g of piperidine were added to a solution of 10 g of (R,S) α-cyano-3-phenoxybenzyl 2,2-dimethyl-3R-(2,2-dibromovinyl)-cyclopropane-1R-carboxylates used in Example 23 in 25 ml of isopropanol and the mixture was stirred at 20° C. for 18 hours and was then vacuum filtered. The recovered product was washed with isopropanol and dried to obtain 8.6 g of the ester of the (S) alcohol identical to the product of Example 23.

EXAMPLE 27

Using the process of Example 26 but with 1.66 g of diisopropylamine as the base, 10 g of the ester of the (R,S) alcohol were reacted to obtain 8.85 g of the ester of the (S) alcohol of the same quality as in Example 23.

EXAMPLE 28

Using the procedure of Example 26 but with 2.7 g of ephedrine as the base, and stirring at 20° C. for 24 hours 10 g of the ester of the (R,S) alcohol were reacted to obtain 8.7 g of the ester of the (S) alcohol of the same quality as in Example 23.

EXAMPLE 29

Using the procedure of Example 23 but with 4.4 g of triethylenediamine as the base and stirring for 72 hours at 20° C., 10 g of the ester of the (R,S) alcohol were reacted to obtain 7.5 g of the ester of the (S) alcohol of the same quality as in Example 23.

EXAMPLE 30

Using the procedure of Example 23 but with 0.23 g of potassium tert.-butylate as the base and stirring at 20° C. for 18 hours, 10 g of the ester of the (R,S) alcohol were reacted to obtain 7.7 g of the ester of the (S) alcohol of the same quality as in Example 23.

EXAMPLE 31

Using the procedure of Example 23 but with 0.34 g of sodium isopropylate as the base and stirring at 20° C. for 24 hours, 10 g of the ester of the (R,S) alcohol were reacted to obtain 7.3 g of the ester of the (S) alcohol of the same quality as in Example 23.

EXAMPLE 32

0.84 g of benzylamine were added to a solution of 10 g of (R,S) α-cyano-3-phenoxybenzyl 2,2-dimethyl-3R-(2,2-dibromovinyl)-cyclopropane-1R-carboxylate as used in Example 23 in 25 ml of isopropanol containing 3.5% water and the mixture was stirred at 20° C. for 23 hours. The mixture was vacuum filtered and the recovered product was crystallized from isopropanol to obtain 8.25 g of the ester of the (S) alcohol with a specific rotation of $[\alpha]_D^{20} = +57°$ (c = 4% in toluene).

EXAMPLE 33

Using the procedure of Example 23 but with 1.20 g of n-butylamine as the base and stirring at 20° C. for 24 hours, 10 g of the ester of the (R,S) alcohol were reacted to obtain 9.0 g of the ester of the (S) alcohol of the same quality as in Example 23.

EXAMPLE 34

Using the procedure of Example 23 but with 1.20 g of sec-butylamine as the base, 10 g of the ester of the (R,S) alcohol were reacted to obtain 9.1 g of the ester of the (S) alcohol of the same quality as in Example 23.

EXAMPLE 35

Using the procedure of Example 30 but with 0.64 ml of an aqueous solution of 40% tertrabutyl ammonium hydroxide as the base and stirring at 20° C. for 24 hours, 10 g of the ester of (R,S) alcohol were reacted to obtain 8.4 g of the ester of the (S) alcohol of the same quality as in Example 23.

EXAMPLE 36

10 g of Amberlite IRA 400 resin (20/50 mesh size; strongly basic copolymer of styrene and divinylbenzene containing quaternary ammonium functions previously washed with perchloric acid diluted 1/3 and then was washed with water until neutral, then with N sodium hydroxide and then with water) were added to a solution of 10 g of (R,S) α-cyano-3-phenoxybenzyl 2,2-dimethyl-3R-(2,2-dibromovinyl)-cyclopropane-1R-carboxylate in 25 ml of isopropanol. The mixture was stirred for 24 hours at 20° C. and was then vacuum filtered. The recovered product which was a mixture of resin and the ester of the (S) alcohol was added to methylene chloride and the mixture was stirred and filtered. The filtrate was evaporated to dryness to obtain 7.8 g of the ester of the (S) alcohol of the same quality as in Example 23.

EXAMPLE 37

Using the procedure of Example 36 but with 10 g of Amberlite IR 45 (mesh size of 20/50 — weakly basic copolymer of styrene and divinylbenzene containing primary, secondary and tertiary amino groups) and stirring for 72 hours at 20° C., 10 g of the ester of the (R,S) alcohol were reacted to obtain 8.1 g of the ester of the (S) alcohol identical to that of Example 23.

EXAMPLE 38

Using the procedure of Example 36 but with 10 g of Dowex AG1X8 (mesh size of 200/400 — anion exchange resin characterized as a strong base in which the active group is trimethyl benzyl ammonium group and contains 8% of divinyl benzene) and stirring for 72 hours at 20° C., 10 g of the ester of the (R,S) alcohol were reacted to obtain 7 g of the ester of the (S) alcohol identical to that of Example 23.

EXAMPLE 39

Using the procedure of Example 36 but with 10 g of liquid Amberlite LA1 (high molecular weight amine — viscosity of 72 cps at 25° C.) as the base, 10 g of the ester of the (R,S) alcohol were reacted and stirred for 72 hours to obtain 8.9 g of the ester of the (S) alcohol identical to that of Example 23.

EXAMPLE 40

Using the procedure of Example 36 but with 3.75 g of liquid Amberlite LA2 (viscosity of 18 cps at 25° C.) as the base and 18 hours of stirring at 20° C., 10 g of the ester of the (R,S) alcohol was reacted to obtain 8.1 g of the ester of the (S) alcohol identical to that of Example 23.

EXAMPLE 41

Using the procedure of Example 36 but with 3.5 ml of isopropanol containing 3.5% of water and stirring for 24 hours at 20° C., 10 g of the ester of the (R,S) alcohol were reacted to obtain 8.95 g of the ester of the (S) alcohol of the same quality as in Example 23.

EXAMPLE 42

An insecticidal composition was prepared from 25 g/l of (S) α-cyano-3-phenoxybenzyl 2,2-dimethyl-3R-(2,2-dichlorovinyl)-cyclopropane-1R-carboxylate, 10 g/l of 2,6-ditert.-butyl-p-cresol, 50 g/l of Emcol H 300B, 20 g/l of Emcol H 500B and 786 g/l of Supersol [a commercial mixture of aromatic solvents]. The Emcol products are surface active agents which are mixtures of calcium salts of alkyl benzene sulfonates (anionic part) and polyoxyethylene ethers (non-ionic part)

INSECTICIDAL ACTIVITY

A. Activity against houseflies

The insecticidal tests were effected on domestic flies of mixed sexes by applying a topical solution of 1 μl of acetone solution of (S) α-cyano-3-phenoxybenzyl 2,2-dimethyl-3R-(2,2-dichlorovinyl)-cyclopropane-1R-carboxylate (product A) to the dorsal thorax of the flies. 50 flies were used for each test and the results were determined as the $LD_{50}$, dose at which 50% of the flies were dead 24 hours after treatment. The results are reported in Table I.

TABLE I

| Dose in ng of product A | % dead after 24 hours | $LD_{50}$ |
|---|---|---|
| 5 | 93.3 | |
| 3.75 | 83.2 | |
| 2.5 | 68.0 | 1.6 ng |
| 1.25 | 34.5 | |
| 0.625 | 10.0 | |

The results of Table I show that the product A has a very high insecticidal activity against houseflies.

B. Activity against Spodoptera Littoralis larvae

This test was effected by topical application of 1 μl of an acetone solution of product A on the dorsal thorax of each larva and for each test, 15 caterpillers of Spodoptera Littoralis in the 4th larva stage were used. After treatment, the individuals were placed in an artificial nutritive media (Poitot medium) and the number of dead caterpillers was determined 24 and 48 hours after the treatment to determine the $LD_{50}$ dose. The results are reported in Table II.

TABLE II

| Dose of A in ng | % dead after 24 h | 48 h | $LD_{50}$ at 48 h |
|---|---|---|---|
| 1.25 | 95.6 | 97.8 | |
| 0.625 | 80.0 | 82.2 | 0.3 ng |
| 0.3125 | 48.9 | 62.2 | |
| 0.1562 | 20.5 | 27.3 | |

Various modifications of the compounds and method of the invention may be made without departing from the spirit or scope thereof and it should be understood that the invention is to be limited only as defined in the appended claims.

We claim:
1. A process for the preparation of an ester of a chiral (A) acid and (S) α-cyano-3-phenoxybenzyl alcohol comprising reacting an ester of chiral (A) acid with α-cyano-3-phenoxybenzyl alcohol of the formula

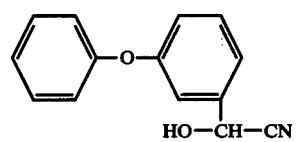

B in its optically active (R) form or a racemic (R,S) mixture or a mixture of esters of said (R) alcohol and (S) alcohol in non-equimolecular proportions with a base selected from the group consisting of ammonium hydroxide, primary, secondary and tertiary amines, quaternary ammonium compounds, liquid amines of high molecular weight, ion exchange resins of a basic character and a catalytic amount of a strong base in at least one solvent in which the ester of the (R) alcohol is soluble and in which the ester of the (S) alcohol is insoluble and recovering from the resulting medium the chiral (A) acid ester of the (S) alcohol which is insoluble.

2. The process of claim 1 wherein the basic agent is selected from the group consisting of ammonium hydroxide, secondary and tertiary amines and a catalytic amount of a strong base.

3. The process of claim 2 wherein the chiral (A) acid is selected from the group consisting of an acid with one asymetric carbon atom and an acid with 2 asymetric carbon atoms.

4. The process of claim 1 wherein the chiral (A) acid is selected from the group consisting of an acid with one asymetric carbon atom and an acid with 2 asymetric carbon atoms and the basic agent is selected from the group consisting of primary amines, quaternary ammonium compounds, high molecular weight liquid amines and ion exchange resins of a basic character.

5. The process of claim 2 wherein the chiral (A) acid is a cyclopropane carboxylic acid with 2 asymetric carbon atoms in the ring.

6. The process of claim 5 wherein the chiral (A) acid is a cis or trans optically active cyclopropane carboxylic acid of the formula

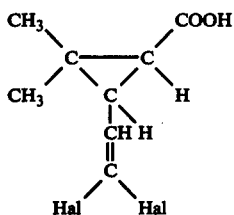

wherein Hal is chlorine or bromine.

7. The process of claim 1 wherein the chiral (A) acid is a cis or trans, optically active cyclopropane carboxylic acid of the formula

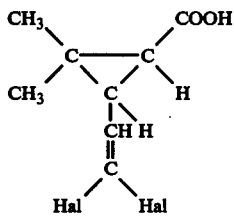

wherein Hal is chlorine or bromine and the basic agent is selected from the group consisting of primary amines, quaternary ammonium compounds, high molecular weight liquid amines and ion exchange resins of a basic character.

8. The process of claim 2 wherein the chiral (A) acid is selected from the group consisting of 2,2-dimethyl-3R-(2,2-dibromovinyl)-cyclopropane-1R-carboxylic acid and 2,2-dimethyl-3R-(2,2-dichlorovinyl)-cyclopropane-1R-carboxylic acid.

9. The process of claim 1 wherein the chiral (A) acid is selected from the group consisting of 2,2-dimethyl-3R-(2,2-dibromovinyl)-cyclopropane-1R-carboxylic acid and 2,2-dimethyl-3R-(2,2-dichlorovinyl)-cyclopropane-1R-carboxylic acid and the basic agent is selected from the group consisting of primary amines, quaternary ammonium compounds, high molecular weight liquid amines and ion exchange resins of a basic character.

10. The process of claim 2 wherein the basic agent is selected from the group consisting of ammonium hydroxide, triethylamine, diethylamine, morpholine, pyrrolidine, piperidine and a catalytic amount of a strong base selected from the group consisting of sodium hydroxide, potassium hydroxide, alkali metal alcoholates, alkali metal amides and alkali metal hydrides.

11. The process of claim 2 wherein the basic agent is selected from the group consisting of diisopropylamine, ephedrine, triethylenediamine and catalytic amounts of potassium tert.-butylate and sodium isopropylate.

12. The process of claim 1 wherein the basic agent is selected from the group consisting of benzylamine, n-butylamine, sec.-butylamine, tetrabutyl ammonium hydroxide, high molecular weight amines insoluble in water and ion exchange resins with a strongly basic character containing amines or quaternary ammonium groups.

13. The process of claim 1 wherein the solvent is selected from the group consisting of acetonitrile, alkanols and mixtures of alkanols and petroleum ether.

14. The process of claim 2 wherin the solvent is selected from the group consisting of acetonitrile, alkanols and mixtures of alkanols and petroleum ether.

15. The process of claim 2 wherein the chiral (A) acid is 2,2-dimethyl-3R-(2,2-dibromovinyl)-cyclopropane-1R-carboxylic acid.

16. The process of claim 15 wherein the solvent is selected from the group consisting of acetonitrile, alkanols and mixtures of alkanols and petroleum ether and the basic agent is selected from the group consisting of ammonium hydroxide, triethylamine, diethylamine, morpholine, pyrrolidine, piperidine and a catalytic amount of a strong base selected from the group consisting of sodium hydroxide, potassium hydroxide, alkali metal alcoholates, alkali metal amides and alkali metal hydrides.

17. The process of claim 15 wherein the solvent is selected from the group consisting of acetonitrile, alkanols and mixtures of alkanols and petroleum ether and the basic agent is selected from the group consisting of diisopropylamine, ephedrine, triethylenediamine and catalytic amounts of potassium tert.-butylate and sodium isopropylate.

18. The process of claim 1 wherein the chiral (A) acid is 2,2-dimethyl-3R-(2,2-dibromovinyl)-cyclopropane-1R-carboxylic acid.

19. The process of claim 18 wherein the basic agent is selected from the group consisting of benzylamine, n-butylamine, sec.-butylamine, tetrabutyl ammonium hydroxide, high molecular weight amines insoluble in water and ion exchange resins with a strongly basic character containing amines or quaternary ammonium groups.

20. The process of claim 2 wherein the starting ester is (R) α-cyano-3-phenoxybenzyl 2,2-dimethyl-3R-(2,2-dibromovinyl)-cyclopropane-1R-carboxylate.

21. The process of claim 1 wherein the starting ester is (R) α-cyano-3-phenoxybenzyl 2,2-dimethyl-3R-(2,2-dibromovinyl)-cyclopropane-1R-carboxylate and the basic agent is selected from the group consisting of primary amines, quaternary ammonium compounds, high molecular weight liquid amines and ion exchange resins of a basic character.

22. The process of claim 2 wherein the chiral (A) acid is 2,2-dimethyl-3R-(2,2-dichlorovinyl)-cyclopropane-1R-carboxylic acid.

23. The process of claim 1 wherein the chiral (A) acid is 2,2-methyl-3R-(2,2-dichlorovinyl)-cyclopropane-1R-carboxylic acid.

24. The process of claim 2 wherein the starting ester is (R) α-cyano-3-phenoxybenzyl 2,2-dimethyl-3R-(2,2-dichlorobinyl)-cyclopropane-1R-carboxylate.

25. The process of claim 1 wherein the starting ester is (R) α-cyano-3-phenoxybenzyl 2,2-dimethyl-3R-(2,2-dichlorovinyl)-cyclopropane-1R-carboxylate and the basic agent is selected from the group consisting of primary amines, quaternary ammonium compounds, high molecular weight liquid amines and ion exchange resins of a basic character.

* * * * *